United States Patent [19]

Klein et al.

[11] Patent Number: 4,925,945
[45] Date of Patent: May 15, 1990

[54] CERTAIN -N-(AMINO BENZOYL)-N'-(PYRIDYLDITHIOALK-ANOYL)-HYDRAZINES AND DERIVATIVES THEREOF

[75] Inventors: Christian Klein, Weilheim; Peter Kirch, Rott, both of Fed. Rep. of Germany

[73] Assignee: Boehringer Mannheim GmbH, Mannheim, Fed. Rep. of Germany

[21] Appl. No.: 327,304

[22] Filed: Mar. 22, 1989

[30] Foreign Application Priority Data

Mar. 24, 1988 [DE] Fed. Rep. of Germany ....... 3809986

[51] Int. Cl.$^5$ ..................... C07D 213/71; C07K 15/00
[52] U.S. Cl. .................................... 546/292; 530/323; 530/345; 530/390; 562/445
[58] Field of Search ............................... 546/292, 291

[56] References Cited

U.S. PATENT DOCUMENTS 4,647,655 3/1987 Axen et al. ........................... 530/390

FOREIGN PATENT DOCUMENTS 0196007 10/1986 European Pat. Off. ............. 546/281
0240200 10/1987 European Pat. Off. ............ 546/261
1597756 9/1981 United Kingdom ................. 546/281

Primary Examiner—Alan L. Rotman
Attorney, Agent, or Firm—Felfe & Lynch

[57] ABSTRACT

The present invention provides compounds of the general formula:

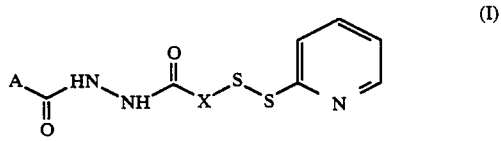

(I)

wherein A is an amine-substituted aromatic radical and X is a hydrocarbon radical containing up to 10 carbon atoms.

The present invention also provides a process for the preparation of these compounds.

Furthermore, the present invention is concerned with the use of the compounds for introducing SH groups into tyrosine.

3 Claims, No Drawings

CERTAIN -N-(AMINO BENZOYL)-N'-(PYRIDYLDITHIOALKANOYL)-HYDRAZINES AND DERIVATIVES THEREOF

The present invention is concerned with new pyridine derivatives, a process for the preparation thereof and with the use thereof.

A series of reagents are known for the introduction of reactive groups into proteins which are described, for example, in "Practice and Theory of Enzyme Immunoassays", P. Tijssen, ed. R. H. Burdon, P. H. von Knippenberg, pub. Elsevier-Verlag, 1985. Such reagents include, for example, 2-iminothiolane (Jue et al., Biochemistry, 17, 5399–5405/1978), N-succinimidyl-3-(2-pyridyldithio)-propionate (Carlsson et al., Biochem. J., 173, 723–737/1978), acetylmercaptosuccinic acid anhydride (Klotz and Heiney, Arch. Biochem. Biophys., 96, 605–612/1962) and S-acetylmercaptoacetic acid N-hydroxysuccinimide ester (R. Julian et al., Anal. Biochem., 132, 68–73/1962). Such compounds react with free amino groups of the protein and can, therefore, only introduce reactive groups into proteins or peptides which have free amino groups, such as the ε-amino groups of lysine, or N-terminal amino groups. However, there are proteins in which few or no reactive amino groups are accessible.

A reagent with which an SH-reactive group can be coupled to tyrosine of proteins or peptides has been described by Duncan et al., J. Immunol. Methods, 80, 137–140/1985. However, this reagent must be used in great excess so that side reactions can take place to a considerable extent.

Therefore, it is the object of the present invention to provide bifunctional compounds which contain a group which can be coupled to tyrosine and in the case of the binding of which to proteins or peptides side reactions only take place to a small extent.

Thus, according to the present invention, there are provided compounds of the general formula:

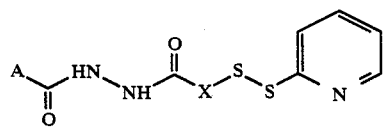

(I)

wherein A is an amine-substituted aromatic radical and X is a hydrocarbon radical containing up to 10 carbon atoms.

X is preferably a hydrocarbon radical containing up to 6 carbon atoms and is especially preferably an ethyliden radical.

The amine-substituted aromatic radical A can be converted, for example, by known methods into a diazonium salt which in turn can easily bind to the aromatic ring of tyrosine or of a tyrosine derivative, whereafter, by reduction, a thiopyridyl radical is split off, an SH group being obtained.

Especially preferred compounds according to the present invention include N-(4-aminobenzoyl)-N'-(pyridyldithiopropionyl)-hydrazine, N-(4-aminobenzoyl)-N'-(pyridyldithioacetyl)-hydrazine, N-(4-aminobenzoyl)-N'-(pyridyldithiobutyryl)-hydrazine, N-(2-aminobenzoyl)-N'-(pyridyldithiopropionyl)-hydrazine, N-(2-aminobenzoyl)-N'-(pyridyldithioacetyl)-hydrazine and N-(2-aminobenzoyl)-N'-(pyridyldithiobutyryl)-hydrazine.

Compounds are also suitable in which the amino-substituted aromatic radical A is additionally substituted by one or more alkyl radicals. The amine substitution can be present one or more times on the aromatic radical A.

Surprisingly, we have found that of the compounds according to the present invention, in the case of the coupling reaction with proteins or peptides, about one third of the amount of reagent used is incorporated so that only about a three fold excess of the reagent has to be used for the reaction.

The present invention also provides a process for the preparation of compounds of general formula (I), wherein a pyridyldithioalkylcarboxylic acid N-hydroxysuccinimide ester containing up to 10 carbon atoms in the alkyl moiety of the carboxylic acid residue is reacted with the hydrazide of an aromatic carboxylic acid which is amine-substituted on the aromatic ring.

Pyridyldithioalkylcarboxylic acid N-hydroxysuccinimide esters are obtained from the corresponding pyridyldithioalkyl carboxylic acids by reaction with N-hydroxysuccinimide and a condensation agent, for example dicyclohexylcarbodiimide, diisopropylcarbodiimide or morpholinoethyl isocyanide.

Starting materials for the pyridyldithioalkylcarboxylic acids are the corresponding mercaptoalkylcarboxylic acids. They are converted into the desired compounds by reaction with 2,2'-pyridyl disulphide.

Preferably, pyridyldithiopropionic acid N-hydroxysuccinimide ester is reacted with the hydrazide of an aromatic carboxylic acid which is amine-substituted on the aromatic ring.

For the preparation of the preferred compound, N-(4-aminobenzoyl)-N'-(pyridyldithiopropionyl)-hydrazine, pyridyldithiopropionic acid N-hydroxysuccinimide ester is reacted with p-aminobenzoic acid hydrazide.

The present invention is also concerned with the use of a compound of general formula (I), preferably of N-(4-aminobenzoyl)-N'-(pyridyldithiopropionyl)-hydrazine, for the introduction of an SH group into tyrosine or a tyrosine derivative and especially into tyrosine or a tyrosine derivative bound in a peptide or protein. The compound according to the present invention is thereby bound via the amine substitution of group A to the aromatic ring of the tyrosine and a thiopyridyl radical is split off by reduction, an SH group thereby being formed.

In a preferred embodiment of the present invention, the amino group of the radical A is diazotised in known manner before the reaction with tyrosine or a tyrosine derivative and the liberation of the SH group is brought about by the action of a reducing agent. The reducing agent is thereby preferably a thiol, for example dithiothreitol.

Examples of suitable tyrosine derivatives include thyroxine and triiodothyronine. Examples of proteins into which an SH group can be introduced according to the present invention include RSA, IgG and HBsAg (hepatitis-B surface antigen).

According to the present invention, it is possible to introduce SH groups into tyrosine side chains. In the case of the preferred incorporation after diazotisation of the compound according to the present invention, a diazo group results so that the rate of incorporation can be determined by simple UV measurement. According to the present invention, the liberation of the SH group takes place selectively only after the addition of the reducing agent, which can also be monitored by UV measurement.

According to the present invention, it is also possible to incorporate an SH reactive group, namely of a pyridyldithio group, i.e. a group which can react with SH groups. The reduction step then becomes unnecessary in the case of the preparation.

The following Examples are given for the purpose of illustrating the present invention:

EXAMPLE 1

Synthesis of N-(4-aminobenzoyl)-N'-(pyridyldithiopropionyl)-hydrazine 242 mg. p-Aminobenzoic acid hydrazide are taken up in 20 ml. dioxan/water (3:1 v.v) and 500 mg. pyridyldithiopropionic acid N-hydroxysuccinimide ester are added thereto. The reaction mixture is stirred for 4 hours at ambient temperature, then evaporated to dryness in a vacuum and the residue recrystallised from methanol. The crystallisate is filtered off with suction, washed with chloroform and dried in a vacuum over anhydrous calcium chloride. Yield: 500 mg. (89% of theory).

$^1$H-NMR ([D]$_6$-DMSO/CD$_3$COOH): δ=2.66 (t, J=6.6 Hz, 2H); 3.09 (t, J=6.6 Hz, 2H); 6.6 (d, J=7.2 Hz, 2H); 7.22 (q, J=4.5 Hz, 1H); 7.63 (d, J=7.2 Hz, 2H); 7.81 (m, 2H); 8.47 ppm (d, J=4.5 Hz, 1H).

EXAMPLE 2

Coupling of N-(4-aminobenzoyl)-N'-(pyridyldithiopropionyl)-hydrazine to sheep immunoglobulin (a) Preparation of the reagent solution 5 mg. N-(4-aminobenzoyl)-N'-(pyridyldithiopropionyl)-hydrazine (14.4 μmol) are dissolved at 0° C. in 0.2 ml. 5N hydrochloric acid. To this are added 10 μl of an aqueous solution of sodium nitrite (220 mg./ml.), followed by stirring for 10 minutes at 0° C. 10 μl. 2M urea are added thereto and the reaction mixture further stirred for 10 minutes at 0° C. The reaction solution is diluted with ice-cold water to 2 μmol/ml. and then used immediately.

(b) Coupling to sheep immunoglobulin

500 μl. sheep immunoglobulin (c=20 mg./ml.) in 0.1M borate buffer (pH 9.2) are mixed with 500 μl. 0.8M borate buffer (pH 9.2). At 0° C. there are added thereto alternatingly in at least 5 portions: 500 μl. 0.14M sodium hydroxide solution and 50 μl. of the above-described reagent solution. 15 mol of reagent are thus used per mol of immunoglobulin.

Incubation is carried out for 20 minutes at 0° C. and thereafter for 20 minutes at 25° C., followed by desalination over Sephadex G 25.

For the determination of the amount M of bound reagent, the extinction (OD) is determined at 420 nm and calculated according to the following formula:

$$M \text{ (mmol/l)} = \frac{OD_{420}}{3000}$$

According to the determination of the protein concentration, there is obtained a rate of incorporation of 4.8:1.

(c) Liberation of the SH groups with dithiothreitol

The protein solution is adjusted with 2M acetic acid to pH 4.5 and mixed with dithiothreitol to 20 mM. The mixture is incubated for 20 minutes at 25° C. By means of extinction measurement at 343 nm (absorption of the liberated thiopyridone), there are determined the liberated SH groups. The extinction increase (OD$_{343}$) divided by 8.08 gives the concentration of SH groups in μmol/ml. There is obtained a degree of loading of 5 SH groups/molecule IgG.

Analogously, in the case of HBsAg (hepatitis-B surface antigen) and HBeAg (hepatitis-B-e antigen), there can be incorporated 0.2 to 2 mole SH groups/mole of protein, depending upon the excess of reagent used. As a rule, one third of the reagent provided is incorporated.

It will be understood that the specification and examples are illustrative but not limitative of the present invention and that other embodiments within the spirit and scope of the invention will suggest themselves to those skilled in the art.

We claim:

1. A compound of the formula:

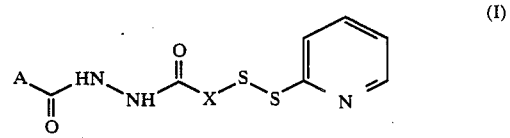

wherein A is an amino-substituted phenyl radical and X is a C$_1$–C$_{10}$ hydrocarbon.

2. An N-(4-Aminobenzoyl)-N'-(pyridyldithiopropionyl)-hydrazine according to formula I of claim 1.

3. A compound according to formula I of claim 1 selected from the group consisting of N-(4-aminobenzoyl)- N'(pyridyldithioacetyl)-hydrazine, N-(4-aminobenzoyl)- N'-(pyridyldithiobutyryl)-hydrazine, N-(2-aminobenzoyl)- N'-(pyridyldithiopropionyl)-hydrazine, N-(2-aminobenzoyl)- N'-(pyridyldithioioacetyl)-hydrazine, and N-(2-aminobenzoyl)- N'-(pyridyldithiobutyryl)-hydrazine.

* * * * *

UNITED STATES PATENT AND TRADEMARK OFFICE
CERTIFICATE OF CORRECTION

PATENT NO. : 4,925,945
DATED : May 15, 1990
INVENTOR(S) : Klein et al.

It is certified that error appears in the above-identified patent and that said Letters Patent is hereby corrected as shown below:

Col. 1, line 54: change "ethyliden" to -- ethylidene --.

Col. 3, line 27: change "8=2.66" to -- $\delta$ =2.66 --.

Signed and Sealed this

Eleventh Day of August, 1992

*Attest:*

DOUGLAS B. COMER

*Attesting Officer*     *Acting Commissioner of Patents and Trademarks*